(12) United States Patent
Das et al.

(10) Patent No.: US 6,864,200 B2
(45) Date of Patent: Mar. 8, 2005

(54) SELECTIVATED METALLOSILICATE CATALYST COMPOSITE FOR ALKYLAROMATIC CONVERSION, PROCESS FOR THE PREPARATION THEREOF, AND USE THEREOF IN HYDROCARBON CONVERSION

(75) Inventors: Jagannath Das, Gujarat (IN); Anand Bhimrao Halgeri, Gujarat (IN)

(73) Assignee: Indian Petrochemicals Corporation Limited, Gujarat (IN)

( * ) Notice: Subject to any disclaimer, the term of this patent is extended or adjusted under 35 U.S.C. 154(b) by 0 days.

(21) Appl. No.: 09/935,991

(22) Filed: Aug. 23, 2001

(65) Prior Publication Data

US 2002/0151758 A1 Oct. 17, 2002

(30) Foreign Application Priority Data

Jan. 23, 2001 (IN) ..................................... 76/MUM/2001

(51) Int. Cl.$^7$ ............................................... B01J 29/06
(52) U.S. Cl. .......................... 502/63; 502/60; 502/61; 502/64; 502/66; 502/71; 502/74; 502/77; 502/85
(58) Field of Search .......................... 502/60, 61, 63, 502/64, 66, 71, 74, 77, 85

(56) References Cited

U.S. PATENT DOCUMENTS

| 3,698,157 A | | 10/1972 | Allen et al. | |
|---|---|---|---|---|
| 3,702,886 A | | 11/1972 | Argauer et al. | |
| 4,002,697 A | | 1/1977 | Chen | |
| 4,060,568 A | | 11/1977 | Rodewald | |
| 4,127,616 A | | 11/1978 | Rodewald | |
| 4,283,306 A | | 8/1981 | Herkes | |
| 4,390,414 A | * | 6/1983 | Cody | 208/111.15 |
| 4,402,867 A | | 9/1983 | Rodewald | |
| 5,349,113 A | | 9/1994 | Chang et al. | |
| 5,349,114 A | | 9/1994 | Lago et al. | |
| 5,365,004 A | * | 11/1994 | Beck et al. | 585/475 |
| 5,476,823 A | * | 12/1995 | Beck et al. | 502/60 |
| 5,495,059 A | | 2/1996 | Beck et al. | |
| 5,530,170 A | * | 6/1996 | Beck et al. | 585/467 |
| 5,541,146 A | | 7/1996 | Chang et al. | |
| 5,552,357 A | | 9/1996 | Lago et al. | |
| 5,567,666 A | * | 10/1996 | Beck et al. | 502/71 |
| 5,574,199 A | | 11/1996 | Beck et al. | |
| 5,602,066 A | * | 2/1997 | Beck et al. | 502/64 |
| 5,609,751 A | * | 3/1997 | Wall | 208/133 |
| 5,612,270 A | * | 3/1997 | Beck et al. | 502/64 |
| 5,625,104 A | * | 4/1997 | Beck et al. | 585/475 |
| 5,726,114 A | * | 3/1998 | Chang et al. | 502/64 |
| 5,990,365 A | | 11/1999 | Chang et al. | |
| 6,066,770 A | * | 5/2000 | Wu et al. | 585/475 |
| 6,084,096 A | * | 7/2000 | Li et al. | 544/352 |

OTHER PUBLICATIONS

Elementary Principles of Chemical Processes, Felder et al., 1978, p. 106.*
Shapeselective Catalysis in Industrial Application, Eds Chen, Garwood, +Dwyer (19890.
Reading et al "Selective Alkylation of Toluene with Methanol to produce Para–Xylene" IN: Journal of Catlysis, vol. 67, No. 1, 1981, Academic Press, Eds Hall et al.

* cited by examiner

Primary Examiner—Kiley Stoner
Assistant Examiner—Christina Ildebrando
(74) Attorney, Agent, or Firm—Pillsbury Winthrop LLP

(57) ABSTRACT

A repeated "soak and dry" selectivation process for preparing a modified metallosilicate catalyst composite is disclosed comprising of a mixture of amorphous silica, alumina and a pore size controlled metallosilicate useful for alkylaromatic conversion. The process comprises (a) contacting an intermediate pore metallosilicate with an organosilicon compound in a solvent for a specific duration and then recovering the solvent, (b) combining the organosilicon compound treated metallosilicate with water and then drying the catalyst, (c), repeating the steps a) and b) above and (d) calcining the catalyst in an oxygen containing atmosphere sufficient to remove the organic material and deposit siliceous matter on the metallosilicate. In a another embodiment, when the organosilicon compound is water soluble, step (b) may be avoided.

43 Claims, No Drawings

SELECTIVATED METALLOSILICATE CATALYST COMPOSITE FOR ALKYLAROMATIC CONVERSION, PROCESS FOR THE PREPARATION THEREOF, AND USE THEREOF IN HYDROCARBON CONVERSION

FIELD OF THE INVENTION

The present invention relates to a method of preparing the modified metallosilicate and a modified metallosilicate so prepared. This invention also relates to shape-selective hydrocarbon conversion processes using the modified metallosilicate catalyst prepared in accordance with this invention.

BACKGROUND OF INVENTION

It is well known that dimethylbenzenes, i.e. xylenes has three isomers, namely para-, meta- and ortho. The para-isomer is industrially more important than that of the other two isomers.

1,4-dimethylbenzene, i.e. para-xylene is useful in the manufacture of terephthalic acid that is an intermediate in the manufacture of polyester fibre. The production of para-xylene is a multi million dollar business, and the large scale of the economies involved mean that even a small improvement in these processes results in improving the cost effectiveness of the process. Dimethylbenzenes, i.e. xylenes can be conveniently prepared by employing Friedel Crafts alkylation catalyst like $AlCl_3$, HCl, HF, $BF_3$ etc. However, these catalysts are corrosive in nature. In addition, it is impossible to avoid loss of raw material through multiple alkylations and other side reactions. Further, the xylenes are produced in thermodynamic equilibrium composition, e.g. para-; meta-; ortho-=24:52:24. These three xylene isomers have very close boiling point to each other, the relative volatility is nearly one. Hence separation of para-xylene is difficult and tremendously expensive.

Mobil Oil Corporation discovered a new type of zeolite known as ZSM-5. The method of preparation of this zeolite is described in U.S. Pat. No. 3,702,886. The crystal structure of ZSM-5 zeolite has a specific order of arrangement and is a porous aluminosilicate material. The specific pore size and regular channels have the capability to absorb or allow entry of such molecules as are smaller in size than that of the pore-opening, while rejecting larger molecules. Hence, it is frequently referred as 'molecular sieve'. In addition, ZSM-5 zeolite also exhibits property of shape-selectivity. The phenomenon of shape selectivity has been described in detail in "Shape-selective Catalysis in Industrial Application", Vol.36, Mercel Dekker Inc. (1989).

There are many precedents in industry, which make use of these characteristics to conduct chemical reactions. ZSM-5 catalyst is characterized by its selectivity, being able to satisfy the needs for high selectivity to products of different molecules, but its selectivity falls short of expectation in respect of isomers of same kind of product. For instance, when toluene is alkylated with methanol over ZSM-5 catalyst, selectivity for xylenes is very high, but the ratio of isomers of xylenes namely para-, meta- and ortho-, remains near thermodynamic equilibrium composition. The details are reported in J. of Catalysis, Vol.67, page 159 (1981), by W. W. Keading et. al.

Enhancement of para-selectivity, (the fraction of para-isomer in a mixture of para-disubstituted aromatics), by treatment with organosilicon compound is usually referred to in the art as selectivation by silanation. The organosilicon compound is usually known as selectivating agent. The method normally comprises contacting the zeolite with organosilicon compound, separation/removal of solvent (if used), and calcination of zeolite to deposit silica or polymeric silica as a layer on the zeolite.

It is known in the art that the efficiency of silica deposition in order to enhance the selectivity of the zeolite depends on the nature or the kind or the type or the molecular structure of the selectivating agent, i.e. the organosilicon compound employed. The efficiency of silica deposition also depends on the temperature of silanation, the solvents or the carrier for the organosilicon compound, the method or procedure adopted for the selectivation. Pretreatment of the zeolite, i.e. treatment carried out before selectivating the zeolite has also been found to affect the final selectivity of the zeolite. Also post-treatment, i.e. treatment after the selectivating the zeolite have also been described in the art to further improve the selectivity of the zeolite for particular hydrocarbon conversion processes.

Selectivation of zeolites by silanation can be vapour phase or liquid phase. Liquid phase silanation is also referred as ex-situ silanation, or ex-situ selectivation. The zeolite is impregnated with an organosilicon compound dissolved or dispersed in a carrier or solvent followed by calcination of such treated zeolite in an oxygen containing atmosphere under conditions sufficient to remove organic material therefrom and deposit siliceous material on the zeolite. Such ex-situ silanation may result in deposition of at least 1% by weight of siliceous material on the catalyst or zeolite.

Examples of various patents, which teach the ex-situ selectivation of zeolites to enhance para-selectivity are U.S. Pat. No. 3,698,157 (to Allen et. al.), U.S. Pat. No. 4,002,697 (to Chen), U.S. Pat. Nos. 4,127,616 and 4,402,867 (both to Rodewald).

U.S. Pat. No. 3,698,157 (to Allen et al) describes improved chromatographic separation of $C_8$ aromatic mixture for the recovery of para-xylene therefrom using aluminosilicate zeolite H-ZSM-5 modified with octadecyltrichlorosilane.

U.S. Pat. No. 4,002,697 (to Chen) describes preparation of catalyst for xylene manufacture by toluene methylation. Silica modified catalysts employed for the purpose were based on zeolites like ZSM-5, ZSM-11 or ZSM-21 of average crystal size of greater than $0.5\mu$, having surface deactivated by reaction with compounds of nitrogen or silicon, i.e. phenyl carbazole or dimethyldichlorosilane, (which are sufficiently large as to be unable to penetrate the pores of said crystalline aluminosilicate) followed by calcination. Pyridine was employed as a solvent for dimethyldichlorosilane.

U.S. Pat. No. 4,127,616 (to Rodewald) describes catalysts suitable for alkylation of toluene with methanol or ethanol, and toluene disproportionation to obtain selectively the corresponding dialkyl benzene. The catalyst was prepared by deposition of large organosilicon compound e.g. polymeric phenylmethyl silicone or polymeric methylhydrogen silicone on crystalline aluminosilicate H-ZSM-5, followed by calcination.

Silica modified zeolite catalysts have been described in U.S. Pat. No. 4,402,867 (to Rodewald), utilizing aqueous emulsion of methylhydrogen silicone. Such catalysts contain added amorphous silica within the interior of crystalline structure of the zeolite. The organosilicon compound employed in this patent is small enough to enter the pores of the zeolite.

When the ex-situ selectivation process is repeated more than once, the procedure is referred to as multiple selectivation or multiple silanation. In multiple selectivation method, the zeolite is treated at least twice, generally from two to six times with a liquid medium containing the organosilicon compound(s). In the multiple selectivation method, the zeolite is calcined after each impregnation of the organosilicon compound. Examples of multiple silanation are found in U.S. Pat. No. 4,060,568 (to Rodewald), U.S. Pat. Nos. 4,283,306 and 4,449,989 (both to Herkes), U.S. Pat. No. 5,349,114 (to Lago et.al), U.S. Pat. No. 5,495,059 (to Beck et.al), U.S. Pat. No. 5,552,357 (to Lago et.al), U.S. Pat. No. 5,574,199 (to Beck et.al.), U.S. Pat. Nos. 5,726,114 and 5,990,365 (to Chang et.al).

Modification of zeolites described in U.S. Pat. No. 4,060,568 (to Rodewald), comprises preparing crystalline aluminosilicate zeolite catalyst containing amorphous silica within the interior crystalline structure of ZSM-5, by exposing the zeolite to a volatile silane of small molecular dimension, which preferably enters the pores of zeolites, followed by treatment with aqueous ammonia and calcination. The patent describes a catalyst modified by three such treatments with intermediate calcination after each treatment, but provides no description of any enhancement in catalytic selectivity or activity over that which might follow from a single such treatment.

U.S. Pat. Nos. 4,283,306 and 4,449,989 (both to Herkes) also describe methods of modifying crystalline silica catalyst by application of such silica sources as tetraethylorthosilicate (TEOS), or phenyl methyl silicone. Interestingly, performance of the catalyst treated once with a TEOS solution followed by calcination, was better than that of catalyst treated twice with TEOS, and calcined after each treatment. It showed that twice treated catalyst is less active and less selective than the once treated catalyst as measured by methylation of toluene by methanol, indicating that multiple ex-situ silanation confers no advantage over single silanation, rather results in a adverse effect on the para-dialkyl benzene selectivity.

U.S. Pat. No. 5,349,113 (to Chang et al) describes modification of molecular sieve catalyst by treating with substantially aqueous solution of a water soluble organosilicon compound. The method includes concurrent preselectivation and activation to get activated catalyst. The invention also comprises in-situ selectivation by passing a high efficiency para-xylene selectivating agent along with the reactants.

U.S. Pat. No. 5,349,114 (to Lago et al) describes shape-selective hydrocarbon conversion over modified catalytic molecular sieve, which has been modified by (i) being preselectivated with a first silicon containing compound and (ii) subsequently steamed at about 280° C. to 400° C. The patent indicates that the molecular sieve is modified in as-synthesized conditions.

U.S. Pat. No. 5,495,059 (to Beck et al) also describes multiple ex-situ selectivation sequence employing an aqueous carrier for the organosilane compound. Each sequence includes an impregnation of the molecular sieve with the selectivating agent and a subsequent calcination of the impregnated molecular sieve.

Selectivation of molecular sieves has been described during extrusion by agglomerating with organosilicon compound by Chang et al in U.S. Pat. No. 5,541,146.

U.S. Pat. No. 5,552,357 (to Lago et al) describes catalyst modification by treatment of ZSM-5 in as-synthesised or in ion-exchanged form, first by treatment with a silicon containing polymer (propylamine silane polymer) in substantially aqueous solution, followed by calcination. The catalyst was further in-situ selectivated with a second silicon containing compound. For multiple ex-situ selectivation during first stage, i.e. during treatment with propylamine silane polymer, the catalyst was calcined after first treatment and before the second treatment.

Post-treatment of selectivated zeolite with a dealuminizing agent, e.g. monovalent or polyvalent acids, triethylene diamine, urea, ethylenediamine tetra acetic acid, ammonium hexafluorosilicate has been described in U.S. Pat. No. 5,567,666 (to Beck et al).

U.S. Pat. No. 5,574,199 (to Beck et al) describes shape-selective aromatization with a catalytic molecular sieve, which has been modified by multiple ex-situ selectivation method. The method involves exposing the catalytic molecular sieve to at least two selection sequences, each sequence comprising contacting the catalyst with dimethylphenylmethyl polysiloxane in a solvent, followed by calcination.

U.S. Pat. No. 5,726,114 (to Chang et al.) describes a method for modifying intermediate pore catalytic molecular sieve by multiple ex-situ selectivation process by contacting the zeolite with an aqueous emulsion comprising of a silicon containing selectivating agent stabilized with the aid of surfactant and calcining the contacted molecular sieve after each impregnation of silica. The method further comprises of mild steaming of the silica deposited zeolite and also in-situ trim selectivation of the ex-situ selectivated zeolite.

U.S. Pat. No. 5,990,365 describes a method for preparation of a catalyst comprising ZSM-5, rhenium and a selectivating agent e.g. either coke or siliceous material or a combination thereof. The multiple selectivation is carried out by (i) combining a bound form of zeolite with an organosilicon compound (ii) calcining the organosilicon containing material to remove organic material therefrom to deposit siliceous material on the bound ZSM-5 and (iii) repeating steps (i) and (ii) at least once.

While the above mentioned art is of interest, there is no suggestion of enhancing the selectivity of metallosilicate by treatment with aqueous water after the zeolite has been contacted with organosilicon compound and before calcination of the zeolite to improve the silanation efficiency. There is also no suggestion in any of the prior art known to the applicants of multiple silanation of metallosilicates without any intermediate calcination of organosilicon compound treated zeolite after each silanation. Additionally, there is no suggestion of recycling the solvents/carriers for multiple silanation.

Therefore, it would be a significant advance and improvement in the art to overcome the difficulties, disadvantages and deficiencies associated with conventional methods and procedures for modifying catalytic metallosilicates, molecular sieves modified by such methods and the process of shape selective hydrocarbon conversion using such modified catalytic molecular sieves.

The present invention seeks to solves the difficulties, disadvantages, and deficiencies faced by the prior art by providing an improved method for modifying catalytic metallosilicate molecular sieves, and improved processes for shape selective hydrocarbon conversions.

OBJECTS OF THE INVENTION

Accordingly, it is an object of the invention to provide an improved method for silanation of metallosilicate for enhancing the shape-selectivity of the metallosilicate.

Yet another object of the invention is to provide an improved catalytic metallosilicate molecular sieve for shape selective hydrocarbon conversion procedure.

Yet another object of the present invention is to provide an improved multiple silanation procedure and thereby to improve the ease with which the silanation of metallosilicate can be achieved as well as to reduce energy requirement and emission of such methods.

It is still another object of the present invention to improve shape selectivity in hydrocarbon conversion processes over metallosilicates by providing metallosilicates having improved activity and selectivity, wherein the said metallosilicates have been modified by the method described hereinafter.

SUMMARY OF THE INVENTION

The above and other objects are achieved by the novel process of the present invention referred to as "Repeated Soak and Dry, (RSD)" selectivation technique hereinafter. The invention is based on the finding, inter alia, that treatment with aqueous water after the metallosilicate has been treated with organosilicon compound and before calcination, provides unexpectedly improved product, which in turn unexpectedly results in improved shape selective hydrocarbon conversion.

It has also been found that the "RSD" selectivation scheme described above provides unexpectedly better results for shape-selective hydrocarbon conversion regardless of whether the process involves single silanation or multiple silanation modification procedure.

Furthermore, it has also been unexpectedly found that, the present improved multiple silanation scheme for modification of metallosilicate avoiding the intermediate calcination step after each treatment, results in excellent energy savings and lower emissions of industrial application. It also unexpectedly provides results for shape selective hydrocarbon conversion, that are better or at least equivalent to those achieved by employing conventional modification method.

It is an important feature of the invention that it avoids intermediate calcination steps after each silanation step and no prior art known to the applicants envisage multiple silanation process without also envisaging intermediate calcinations after each silanation step.

Another important feature of the invention is combining the organosilicon treated metallosilicate with water prior to calcination, especially, when the organosilicon employed is water-insoluble. Where a water soluble organosilicon compound is employed, it may not always be necessary to specifically combine the treated metallosilicate with water since the zeolite extrudates, after the removal of solvent will normally be wet due to the adherence of some water. However, where a solvent other than water is used and after removal/separation (such as decantation) of the solvent, there is no wetness in the zeolite extrudate, it may be advantageous to add water and dry the product prior to calcination.

It is an important advantage of the present invention that in a multiple silanation procedure, the solvent employed for the first silanation can be recycled for the next silanation.

The present invention provides an improved method for modifying catalytic metallosilicate, the improved catalytic metallosilicate molecular sieve and improved shape selective hydrocarbon processes over modified metallosilicate molecular sieve.

In one aspect, the present invention includes a method for preparing a modified metallosilicate molecular sieve catalyst composite, useful for hydrocarbon conversion to produce para-dialkylbenzene and the said method comprising steps of a) contacting an intermediate pore metallosilicate with an organosilicon compound in a solvent for a specific duration and then removing solvent.
b) combining the organosilicon compound containing metallosilicate with water, and then drying the product.
c) repeating the steps a) and b) any number of times for multiple silanation
d) calcining the product so obtained in an oxygen containing atmosphere under conditions sufficient to remove the organic material to obtain said modified metallosilicate molecular sieve catalyst composite.

Ideally, in this embodiment, the organosilicon compound employed is water insoluble.

The catalyst prepared according to the above method provides better results for shape selective hydrocarbon conversion. In another embodiment of the invention, the organosilane employed is water soluble, and therefore, step (b), i.e., combining with water may be dispensed with.

Accordingly, the present invention also provides a method for preparing a modified metallosilicate molecular sieve catalyst composite, useful for hydrocarbon conversion to produce para-dialkylbenzene and the said method comprising steps of a) contacting an intermediate pore metallosilicate with a water soluble organosilicon compound in a solvent for a specific duration and then removing solvent.
b) drying the product so obtained.
c) repeating the steps a) and b) any number of times for multiple silanation
d) calcining the product so obtained in an oxygen containing atmosphere under conditions sufficient to remove the organic material.

DETAILED DESCRIPTION OF THE INVENTION

The present invention relates to modified metallosilicate molecular sieve catalyst composite, a method of preparation of the modified metallosilicate catalytic molecular sieve composite, and shape selective hydrocarbon processes using the modified metallosilicate composite.

According to a preferred embodiment the modified metallosilicate molecular sieve composite, comprises a mixture of amorphous silica, a pore size regulated metalloaluminosilicate, preferably, aluminosilicate or galloaluminosilicate on an alumina or silica support. The aluminosilicate or galloaluminosilicate is of pentasil family. The method for making aluminosilicates or zeolites of pentasil family is known in the art. In the present invention, the modified aluminosilicate or galloaluminosilicate molecular sieve possesses a silica to alumina ratio of 70 to 700 and a silica to gallium oxides ratio of from 500 to 5000. The catalyst composite may contain 20–80% of a suitable binder, selected from the group of silica, alumina, silica-alumina, alumina sol, silica sol, hydrated alumina etc. In a preferred embodiment the catalyst composite contains 1 to 50% amorphous or polymeric silica or alumina or a mixture thereof.

The present invention will now be described with reference to preparation of a modified metallosilicate for e.g., galloaluminosilicate, purely for the purposes of illustration. It is not the intention of the applicants to exclude other metallosilicates and therefore, references to galloaluminosilicate should be construed accordingly in a wider sense.

The method of preparation of modified galloaluminosilicate of pentasil family comprises (i) contacting the galloaluminosilicate with an organosilicon compound in a solvent and separating the solvent; (ii) optionally combining the organosilicon compound treated galloaluminosilicate with liquid water; (iii) drying the catalyst composite; (iv) repeating steps (i) and (ii) for multiple silanation; and (v) calcining the catalyst under conditions sufficient to remove the organic material and deposit siliceous material on the external surface of the galloaluminosilicate.

The metallosilicate employed herein are of pentasil family, e.g. ZSM-5, ZSM-11 or isomorphous substituted derivatives of those. Preferred metallosilicates are Ga—Al-ZSM-5, Fe—Al-ZSM-5, Ga-ZSM-5, Fe-ZSM-5, Al-ZSM-5 and the like.

The metallosilicate may be employed in the form as-synthesised, or calcined Na-form or in active H-form. Preferred is the H-form of the metallosilicate. The galloaluminosilicate may be in unbound form or may be in a bound form with a binder. The binder may be silica, alumina, or silica alumina and the like. Preferred binder is either silica or alumina.

The organosilicon compound may be either a silicone or a silane or a mixture thereof Examples of organosilicon compounds include phenylmethyl silicone, tetraethoxy silane, 3-aminopropyltriethyoxy silane etc. When a silane is chosen as a selectivating agent, the preferred silanes are alkoxy silanes e.g. tetraethoxy silane, or 3-aminopropyl triethoxy silane. It is also preferred that the kinetic diameter of the selected organosilicon compound is larger than the pore size opening of the metallosilicate which is subjected to modification.

The solvent in which the organosilicon compound is dissolved may be any hydrocarbon liquid, e.g. aliphatic, alicyclic or aromatic hydrocarbons, e.g. $C_5$–$C_8$ hydrocarbons, like pentane, hexane, heptane, octane, cyclopentane, cyclohexane, cycloheptane etc., and benzene, toluene, xylene, or alcohols like methanol, ethanol etc., or mixture thereof A preferred solvent is low boiling in nature as well as non-polar and aprotic one. Water may also be employed when the organosilicon compound is soluble in it. Preferred solvents are cyclohexane, toluene, mixture of toluene and methanol, water etc.

The concentration of the organosilicon compound in the solvent may be in the range of greater than 1 weight percent to less than 99 weight percent, preferably greater than 2% to less than 50%, more preferably, 5% to 25%. The organosilicon compound containing solution is combined with the metallosilicate and treated at a temperature from 0° C. to the boiling point of the solvent for a duration of 0.1 to 24 hours. It may be preferable to soak the metallosilicate in the selectivating solution, i.e. the organosilicon compound containing solution for about 1 hour to 16 hours, or to reflux the combination of metallosilicate and the selectivating agent containing solution for about 0.5 hour to about 12 hours. Subsequently, the solvent is separated by any known means, e.g. by decantation, by filtration or by distillation or by simply allowing for air drying at room temperature and pressure. However, when an organic solvent is employed, it has been found convenient to separate the metallosilicate from the solution by either filtration or distillation. It is preferred to separate the metallosilicate by distillation because such a procedure leaves the metallosilicate substantially free from the organic solvent. In the case of other solvents like water etc, the metallosilicate may be recovered by decantation or filtration.

In an embodiment of the present invention, the solvent employed for dissolving the organosilicon compound is recycled from batch to batch. For example, the solvent employed for silanation of one batch of metallosilicate catalyst, is recovered and reused for the silanation of second batch of metallosilicate and so on. Such a procedure has the advantage of minimizing the liquid effluent to zero level in a commercial unit producing such catalyst.

In another embodiment of the present invention, the metallosilicate is treated with liquid water subsequent to treatment of the metallosilicate with organosilicon compound. The procedure for the treatment may be like addition of the metallosilicate to water or vice-versa. However, it has been found preferable and convenient to add water to the organosilicon compound containing metallosilicate. The amount of water added may be in the range of from 1 to 200 percent, preferably, 2% to 100% of the mass of the metallosilicate, more preferably from 5% to 90% of the mass of metallosilicate, and most preferably, the volume of water added may be somewhat approximately equal to the inter-particle volume of mass of the metallosilicate. The wet extrudates are then dried at a temperature of 10 to 150° C., preferably, 50° C.–150° C. for 1–24 hours, more preferably, at a temperature of 80° C.–130° C. for 2–20 hours.

It has been theorized that the alkoxysilanes, like tetraethoxysilane or 3-aminopropyltriethoxy silane which has a larger kinetic diameter than the pore openings of pentasil metallosilicates, cannot enter into the channels, and hence reacts only with acidic centres which are located on the external surface of the metallosilicates. In a first step, the alkoxysilane molecule gets adsorbed and/or anchored on the external surface acidic sites. In a second step, the reaction between the adsorbed alkoxysilane and the anchored alkoxysilane or between the anchored alkoxysilane molecules takes place leaving out either dimethyl ether or ethyl alcohol. The reaction may be considered as a sort of polymerization accompanied by hydrolysis. While not wishing to be limited by theory, it is believed that the addition of water facilitates the hydrolysis of the anchored alkoxysilane on the external surface of the metallosilicate. This increases the efficiency of deposition of layered siliceous material, when the organosilicon compound containing metallosilicates are calcined for the above said purpose.

If a second selectivation, i.e. multiple silanation is not targeted, the catalyst extrudates are then calcined in an oxygen containing atmosphere, e.g. air, oxygen, or a mixture of nitrogen and oxygen etc. The temperature of the calcination may be in the range of 160° C. to 800° C., preferably in the range of 300° C. to 600° C. and most preferably, at 400° C. to 550° C. The calcination is do atmospheric pressure for 2 to 20 hours, preferably, for 4 to 12 hours.

According to a preferred embodiment of the present invention, the multiple selectivation, i.e. the multiple treatments with the organosilicon compound, are carried out without going for calcination after each selectivation. For example, the second treatment with the organosilicon compound (the selectivating agent) is carried out by repeating the procedures of steps (a), (b) and (c) as described above. The third treatment with the organosilicon compound is carried out by repeating step (a), (b) and (c) above after second treatment. Thus, inventive process of modifying metallosilicate using multiple selectivation scheme as described hereinabove, avoids calcination after each selectivation and can be termed as "Repeated Soak and Dry" (RSD) selectivation method.

Such a process from the commercial point of view, is more energy efficient than that of the conventional procedure for modification of zeolites through multiple silanation, wherein the zeolite is calcined after each treatment with the selectivating agent (i.e., the organosilicon compound). In addition, the emissions released during calcinations are also reduced since the intermediate calcination steps themselves have been dispensed with.

While wishing not to be limited by any theory, it will be appreciated by those skilled in the art that repeated calcination of metallosilicates at high temperatures viz. in the range of more than 500° C. for a long duration may be associated with some loss of the acid sites of the metallosilicates, including the acid sites located at the external surface. Therefore, the multiple silanation on such surfaces of metallosilicates might be less efficient, as compared to those where such loss of acid sites has not taken place. Thus, the present method of multiple silanation without any intermediate calcination step has an added advantage over the conventional procedure.

In another embodiment of the present invention envisaging multiple treatment with organosilicon compound (i.e. the selectivating agent), the organic solvent is recycled from the first treatment with selectivating agent. For example, during the second treatment with organosilicon compound, the solvent recovered from the first treatment is employed. Thus, there is no final liquid effluent in the whole method of preparation of the modified metallosilicate catalyst composite.

Subsequent to the multiple selectivation of the metallosilicate (according the RSD selectivation method), the catalyst is finally calcined in an oxygen containing atmosphere, e.g. air, oxygen, a mixture of nitrogen and oxygen. The temperature of calcination may be in the range of 150° C. to 800° C., preferably, in the range of about 300° C. to 600° C. and most preferably, at about 400° C. to 550° C. The duration of calcination may be in the range of 2 to 10 hours preferably, 3 to 8 hours, at atmospheric pressure.

The present invention also provides a process for shape-selective hydrocarbon conversion, using the modified metallosilicate composite, as described herein above. Such shape-selective reactions include disproportionation or alkylation of mono alkyl benzene to selectively produce para-dialkylbenzene, i.e. disproportionation of toluene to benzene and a mixture of xylenes containing mostly para-xylene. Similarly, ethylbenzene may be disproportionated over the catalyst of present invention to benzene and selectively para-diethylbenzene. Ethylbenzene can be ethylated using ethylene or ethanol to para-diethylbenzene employing the catalyst of the present invention. Toluene can be alkylated with methanol or ethylene or ethanol towards selective formation of para-xylene or para-ethyl toluene. The present catalyst can also be employed for selective de-ethylation of ethylbenzene (i.e. converting ethylbenzene to benzene and ethylene) from a mixture of $C_8$ aromatics containing ethylene benzene and xylene.

As per the process conditions described in U.S. Pat. No. 5,811,613 (to Bhat, Das and Halgeri), the entire content of which is incorporated herein by reference, the present catalyst may be employed for catalyzing vapour phase ethylation of ethylbenzene to produce para-diethylbenzene, at a temperature of 523 K to 773 K, weight hourly space velocity 0 to 10 $h^{-1}$, in the absence of any carrier gas and using steam as co-feed. The process is under commercial operation in India.

As per the process conditions described in European Pat. No. EP 0369078 (to Halgeri et. al.), the entire content of which is incorporated herein by reference, the present catalyst may be employed for conversion of $C_8$ aromatic conversion, particularly for de-ethylation of ethylbenzene.

The present catalyst may also be employed along with the conventional $C_8$ aromatic isomerization catalyst for improved performance in terms of selective and enhanced ethylbenzene conversion of the isomerization feed.

The catalyst of the present invention, prepared by the RSD selectivation method described herein above is particularly useful for selective methylation of toluene to para-xylene. More particularly, the catalyst under the methylation conditions is capable of providing high toluene conversion per pass, while at the same time producing a very high proportion of para-xylene among the total of the xylene isomers. However, it is to be understood that this catalyst may also be employed to catalyze other organic, especially hydrocarbon conversion reactions.

When the catalyst of the present invention is employed for methylation of toluene, the reaction conditions may include a temperature of about 350° C. to 650° C., a pressure of about atmospheric pressure to 30 atmospheres, a toluene to methanol mole ratio of about 0.5:1 to 30:1, weight hourly space velocity 0.1–20 per hour, and a hydrogen or water or hydrogen and water as co-feed. The hydrogen or water or hydrogen and water to total hydrocarbon ratio may be in the range of 0.1 to 10. The use of hydrogen or water or hydrogen and water serves to suppress deactivation of catalyst, thereby increasing the life of catalyst.

The feedstocks for the present toluene methylation process, e.g. toluene and methanol are of commercial grade. Methanol employed for the purpose may contain some water, e.g. 5–15%, or 5–35% or 5–50% water in it, along with the usual commercial impurities in it. Toluene, may optionally contain some hydrocarbons, other than toluene. Such hydrocarbons include benzene, xylenes, ethyltoluenes, and $C_{10}$ aromatics, as well as non-aromatics like paraffins and/or cycloparaffins.

It is to be understood that commercial toluene methylation process may run on a series of reactor wherein the effluent from the first reactor may be put to second reactor with additional input of methanol. Similarly, the effluent from the second reactor may be put to the third reactor along with additional methanol. The amount of remaining (unconverted) toluene from each reactor will depend on the conversion per pass and, accordingly, the concentration of toluene in the feed will decrease from the first reactor to second, and second to third etc. Thus the reactant feed may contain apart from toluene, at least 1 percent to about 26 percent hydrocarbons comprising benzene, xylenes, ethyltoluenes, trimethylbenzenes and $C_{10}$ aromatics.

The invention will now be described in greater detail with the reference to the following examples, which are presented here for the purpose of illustration only and should not be construed as limitative of the scope of the present invention.

EXAMPLE 1 (Comparative)

10 gm. of Ga—Al-ZSM-5 extrudates (containing 65% Ga—Al-ZSM-5 and 35% alumina) in H- form were soaked in a solution containing 3.26 gm tetraethoxy silane in a mixture of 10 ml toluene and 6 ml methanol for 6 hours at room temperature and pressure. The solvents (toluene and methanol) were distilled off and the extrudates were dried in oven at 120° C. overnight. Finally, the tetraethoxy silane treated extrudates were calcined in a flow of air at 535° C. for 8 hours.

Catalytic performance of the modified Ga—Al-ZSM-5 catalyst samples was evaluated in a conventional continuous fixed bed down flow, integral reactor. Feed stream containing toluene and methanol was preheated and put through the reactor using hydrogen/water as carrier gas or hydrogen and water as co-feed. The products were analysed by Gas Chromatograph using capillary column. Reaction conditions and the results are described in Table-1.

EXAMPLE 2

This example shows the effect of addition of liquid water in selectivation procedure. 10 gm of Ga—Al-ZSM-5 extrudates (containing 65% Ga—Al-ZSM-5 and 35% alumina) in H-form were added to a solution of 3.26 gm of tetraethoxy silane in solvent mixture of 10 ml toluene and 6 ml methanol at ambient conditions and allowed to soak for 6 hours. The extrudates were recovered by distilling off the solvents. 5 ml of water was added to the extrudates and left for 30 minutes. The wet extrudates were then dried at 120° C. for 12 hours, and calcined in the same way as described in Example-1. The performance of the catalyst was evaluated for selective toluene methylation and the results are given in Table 1.

TABLE 1

Catalyst performance for Toluene Methylation of Selectivated metallosilicates
Temperature = 450° C., WHSV = 3.5 (based on toluene),
Toluene: Methanol (mole) = 2,

| Example No | Toluene conversion wt %. | Total Xylenes wt %. | para-Xylene selectivity |
|---|---|---|---|
| 1 | 30.1 | 26.0 | 64.1 |
| 2 | 29.3 | 25.0 | 68.9 |

It can be seen that addition of liquid water after the metallosilicate has been treated with tetraethoxy silane, and before calcination, improves the para-xylene selectivity of the catalyst.

EXAMPLE 3 (Comparative)

This example is a comparative example for multiple silanation. The two silanations were carried out by repeating the whole procedure as described in Example-1.

EXAMPLE 4

This example illustrates the improved multiple silanation method of modification with addition of liquid water. The example is given for two silanations, but the technique holds for any number of silanations. The two silanations were carried out by repeating the complete procedure as described in Example-2. Performance of the catalysts of Example 3 and Example 4 are compared in Table 2.

TABLE 2

Catalyst Performance for Toluene Methylation of Selectivated metallosilicates
Temperature = 450° C., WHSV = 3.5 (based on toluene),
Toluene: Methanol (mole) = 2,

| Example No | Toluene Conversion wt %. | Total Xylenes wt %. | Para-Xylene selectivity |
|---|---|---|---|
| 3 | 26.8 | 23 | 77.2 |
| 4 | 25.8 | 22.4 | 85.1 |

Thus, it can be seen that multiple silanation with addition of water after the zeolite had been treated with tetraethoxy silane compound and before calcination at each silanation step, markedly improves the para-xylene selectivity of the catalyst.

EXAMPLE 5

This example illustrates multiple silanation without any calcination after each silanation and also without any water treatment in each silanation step. The example is shown for two silanations but holds good for any number of silanations.

10 gm of Ga—Al-ZSM-5 extrudates (containing 65% Ga—Al-ZSM-5 and 35% alumina) in H- form were treated with tetraethoxy silane in a toluene-methanol mixture as given in Example-1. After removal of solvent by distillation the extrudates were dried at 120° C. in an oven. The dried extrudates were subjected to a second silanation following the procedure just described. Finally, the extrudates were calcined at 535° C. for 8 hours. Performance of theses catalysts for toluene methylation is compared with that of Example 3, where the catalyst was prepared following the conventional technique of calcination after each silanation (See Table 3).

TABLE 3

Catalyst Performance for Toluene Methylation of Selectivated metallosilicates
Temperature = 450° C., WHSV = 3.5 (based on toluene),
Toluene: Methanol (mole) = 2,

| Example No | Toluene Conversion wt %. | Total Xylenes wt %. | Para-Xylene selectivity |
|---|---|---|---|
| 3 | 26.8 | 23 | 77.2 |
| 5 | 26.2 | 23.2 | 76.9 |

Thus, it can be seen that the modification of the metallosilicate through multiple silanation technique, without any intermediate calcination after each selectivation provides equivalent results to those where the same modification was carried out with calcination after each selectivation.

EXAMPLE 6

This example illustrates multiple silanation with water treatment of the organosilicon compound treated metallosilicate and without any intermediate calcination after each silanation step. The example is shown for two silanations but holds good for any number of silanations.

10 gm of Ga—Al-ZSM-5 extrudates (containing 65% Ga—Al-ZSM-5 and 35% alumina) in H-form were soaked for 6 hours in a solution containing 3.26 gm tetraethoxy silane in 10 ml toluene and 6 ml methanol mixture. The solvent was then distilled off and the extrudates were recovered. 5 ml water was added to the extrudates, left for a half an hour and the wet extrudates were dried in an oven at 120° C. The dried extrudates were again treated with tetraethoxy silane and water and dried following the same procedure just described. Finally, the extrudates were calcined at 535° C. for 8 hours. Performance of this catalyst for toluene methylation is compared with that of the catalyst prepared in Example 4 and given in Table 4.

EXAMPLE 7

This example illustrates the reuse of solvents employed for dissolving the organosilicon compound. The procedure followed for the preparation of the catalyst was same as described in Example 6 except that the solvent recovered by distillation during first stage silanation was employed for the second stage silanation. Performance of the catalyst thus prepared is included in Table 4.

TABLE 4

Catalyst Performance for Toluene Methylation of Selectivated metallosilicates
Temperature = 450° C., WHSV = 3.5 (based on toluene),
Toluene: Methanol (mole) = 2,

| Example No | Toluene Conversion wt %. | Total Xylenes wt %. | Para-Xylene selectivity |
|---|---|---|---|
| 4 | 25.8 | 22.4 | 85.1 |
| 6 | 26 | 22.6 | 84.6 |
| 7 | 26.1 | 22.5 | 84.8 |

Thus, it can be seen that the modification of the metallosilicate through multiple silanation technique with addition of water after the metallosilicate had been treated with organosilicon compound and without any intermediate calcination after each selectivation provides equivalent results to those where the same modification was carried out with calcination after each selectivation. Also the repeated use of the recovered solvent does not affect the performance of the catalyst.

EXAMPLE 8 (Comparative)

This example illustrates the preparation of catalyst by multiple silanation with calcination after each silanation employing a water soluble organosilicon compound, e.g., 3-aminopropyltriethoxy silane as selectivating agent.

10 gm of galloaluminosilicate extrudates (containing 65% Ga—Al-ZSM-5 and 35% alumina) in H-form were soaked in a solution containing 3.3 g of 3-aminopropyltriethoxy silane in 6.8 gm of water for six hours. The supernatant liquid was then decanted off and the wet extrudates were then dried at 120° C., and calcined in a flow of air at 535° C. for 20 hours. By repeating the procedure again, the second silanation was completed. Performance of the catalyst for toluene methylation was evaluated and given in Table 5.

EXAMPLE 9

This example shows the benefit of avoiding the intermediate calcination steps for multiple silanation employing 3-aminopropyltriethoxy silane as selectivating agent.

10 gm of galloaluminosilicate extrudates (containing 65% Ga—Al-ZSM-5 and 35% alumina) in H-form were soaked in a solution containing 3.4 gm of 3-aminopropyltriethoxy silane in 6.8 g of water for six hours. The supernatant liquid was then decanted off and the wet extrudates were then dried at 120° C. By repeating the procedure again, the second silanation was completed. Finally, the treated galloaluminosilicate extrudates were calcined in a flow of air at 535° C. for 20 hours. The performance of the catalysts was evaluated for selective toluene methylation and the results are given in Table 5.

TABLE 5

Catalyst performance for Toluene Methylation of Selectivated metallosilicates
Temperature = 450° C., WHSV = 3.5 (based on toluene),
Toluene: Methanol (mole) = 2,

| Example No | Toluene Conversion wt %. | Total Xylenes wt %. | Para-Xylene selectivity |
|---|---|---|---|
| 8 | 25.3 | 21.8 | 73.5 |
| 9 | 26.0 | 21.7 | 74.0 |

EXAMPLE 10 (Comparative)

10 gm of aluminosilicate extrudates (containing 65% Ga—Al-ZSM-5 and 35% alumina) in H-form were soaked in a solution containing 0.72 gm of 3-aminopropyltriethoxy silane in 6 ml water for six hours. The supernatant liquid was then decanted off and the wet extrudates were then dried at 120° C. The dried extrudates were calcined in a flow of air at 535° C. for 8 hours. The calcined extrudates were again soaked in a in a solution containing 0.72 gm of 3-aminopropyltriethoxy silane in 6 ml water for six hours. After removing the excess liquid, the extrudates were dried at 120° C. Finally, the extrudates were again calcined in a flow of air at 535° C. for 8 hours The performance of the catalysts of Example 10 was evaluated for selective toluene methylation and the results are given in Table 6.

EXAMPLE 11

This example shows the benefit of avoiding the intermediate calcination steps for multiple silanation employing 3-aminopropyltriethoxy silane as selectivating agent. The example is given for two silanations but the technique holds for any number of silanations.

10 gm of aluminosilicate extrudates (containing 65% Ga—Al-ZSM-5 and 35% alumina) in H- form were soaked in a solution containing 0.72 gm of 3-aminopropyltriethoxy silane in 6 ml water for six hours. The supernatant liquid was then decanted off and the wet extrudates were then dried at 120° C. The dried extrudates were again soaked in a solution containing 0.72 gm of 3-aminopropyltriethoxy silane in 6 ml water for six hours. After removing the excess liquid, the extrudates were dried at 120° C. Finally, the extrudates were calcined in a flow of air at 535° C. for 8 hours. The performance of the catalysts was evaluated for selective toluene methylation and compared with those of the catalyst prepared in Example 10. The results are given in Table 6.

TABLE 6

Catalyst performance for Toluene Methylation of Selectivated metallosilicates
Temperature = 450° C., WHSV = 3.5 (based on toluene),
Toluene: Methanol (mole) = 2,

| Example No | Toluene Conversion wt %. | Total Xylenes wt %. | Para-Xylene selectivity |
|---|---|---|---|
| 10 | 26.2 | 23.1 | 80.5 |
| 11 | 26.1 | 23.2 | 80.8 |

Obviously, many modifications and variations of the present invention are possible in the light of above teaching.

For example, it is obviously possible in the light of the above description and teaching to prepare a modified metallosilicate catalyst composite by the inventive "RSD" method of making the same as described hereinbefore, so as to achieve para-xylene selectivity as high as more than c.a. 90%, or say 95%, or say more than 99%, while maintaining a reasonably acceptable toluene conversion level. It is, therefore, to be understood that within the scope of the appended claims, the invention may be practiced otherwise than as specifically described.

What is claimed is:

1. A process for preparing a catalyst composite useful for alkylaromatic conversion, the said process comprising:
    a) contacting an intermediate pore metallosilicate with an organosilicon compound in a solvent for a specific duration and then recovering the solvent;
    b) combining the organosilicon compound treated metallosilicate with water and then drying the catalyst;
    c) repeating the steps a) and b) above; and
    d) calcining the catalyst in an oxygen containing atmosphere sufficient to remove the organic material and deposit siliceous matter on the metallosilicate;
    wherein in said process calcining step d) is not repeated after each of step a)+b).

2. A process as claimed in claim 1 wherein said organosilicon compound is water insoluble.

3. A process as claimed in claim 2 wherein the said organosilicon compound is tetraalkoxy silane.

4. A process as claimed in claim 3 wherein the said tetraalkoxy silane is tetraethoxy silane.

5. A process as claimed in claim 1 wherein the said solvent is selected from lower aliphatic alcohols, $C_5$–$C_{10}$ saturated linear or cyclic hydrocarbons, $C_6$–$C_8$ aromatics or mixture thereof.

6. A process as claimed in claim 5 wherein the said solvent is a mixture of toluene and methanol.

7. A process as claimed in claim 1 wherein the concentration of the organosilicon compound in said solvent is in the range of 1 to 25 percent by weight.

8. A process as claimed in claim 1 wherein the said metallosilicate is treated with the organosilicon compound containing solution for 0.5 to 24 hours.

9. A process as claimed in claim 1 wherein the said solvent is recovered after metallosilicate is treated with the organosilicon compound containing solution.

10. A process as claimed in claim 1 wherein amount of said water is in the range of from 1 to 200 percent of the mass of the metallosilicate.

11. A process as claimed in claim 1 wherein the said water combined metallosilicate composite is dried at a temperature of from 10 to 150° C.

12. A process as claimed in claim 11 wherein the said water combined metallosilicate composite is dried at a temperature of from 80 to 130° C.

13. A process as claimed in claim 11 wherein the said wet metallosilicate composite is dried for from 1 to 20 hours.

14. A process as claimed in claim 1 wherein the said water combined metallosilicate composite is dried at a temperature of 50 to 150° C.

15. A process as claimed in claim 1 wherein the step a) and step b) are repeated more than once.

16. A process as claimed in claim 1 wherein the solvent recovered is reused.

17. A process as claimed claim 1 wherein the said calcination is carried out at a temperature in the range of from 160 to 800° C.

18. A process as claimed claim 17 wherein the said calcination is carried out at a temperature in the range of from 300 to 600° C.

19. A process as claimed claim 17 wherein the said calcination is carried out at a temperature in the range of from 400 to 550° C.

20. A process as claimed in claim 1 wherein amount of said water is in the range from 2 to 100% of the mass of the metallosilicate.

21. A process as claimed in claim 1 wherein amount of said water is in the range from 5 to 90% of the mass of the metallosilicate.

22. A process for preparing a catalyst composite useful for alkylaromatic conversion, the said process comprising:
    a) contacting an intermediate pore metallosilicate with a water insoluble organosilicon compound in a solvent and then recovering the solvent;
    b) combining the organosilicon compound treated metallosilicate with water, the amount of water employed being in the range of from 1 to 200 percent of the mass of said metallosillicate;
    c) drying the product from step b) at a temperature in the range of 10 to 150° C.;
    d) repeating the steps a), b) and c) above; and
    e) calcining the product in an oxygen containing atmosphere at a temperature in the range of 160 to 800° C. sufficient to remove the organic material and deposit siliceous matter on the metallosilicate;
    wherein in said process calcining step e) is not repeated after each of step a)+b)+c).

23. A process for preparing a catalyst composite said process comprising:
    a) contacting an intermediate pore metallosilicate with an organosilicon compound in a solvent for a specific duration and then recovering the solvent;
    b) drying the catalyst;
    c) repeating the steps a) and b) above;
    d) calcining the catalyst in an oxygen containing atmosphere sufficient to remove the organic material and deposit siliceous matter on the metallosilicate;
    wherein in said process calcining step d) is not repeated after each of step a)+b).

24. A process as claimed in claim 23 wherein said organosilicon compound used is water soluble.

25. A process as claimed in claim 23 wherein the said solvent is selected from lower aliphatic alcohols, $C_5$–$C_{10}$ saturated linear or cyclic hydrocarbons, $C_6$–$C_8$ aromatics or mixture thereof and water.

26. A process as claimed in claim 23 wherein the said solvent is water.

27. A process as claimed in claim 23 wherein the concentration of the organosilicon compound in said solvent is in the range of 1 to 99% by weight.

28. A process as claimed in claim 23 wherein the said metallosilicate is treated with the organosilicon compound containing solution for 0.5 to 24 hours.

29. A process as claimed in claim 23 wherein the said solvent is recovered after metallosilicate is treated with the organosilicon compound containing solution.

30. A process as claimed claim 23 wherein the said organosilicon compound treated metallosilicate composite is dried at a temperature form 10 to 150° C.

31. A process as claimed in claim 23 wherein said water treated metallosilicate composite is dried for at least 1 hour.

32. A process as claimed in claim 23 wherein the step a) and step b) are repeated at least once.

33. A process as claimed in claim 23 wherein the solvent recovered from the silanation step is reused for further silanation.

34. A process as claimed in claim 23 wherein the said calcination in said oxygen containing atmosphere is carried out at a temperature in the range 160 to 800° C.

35. A process as claimed in claim 23 wherein the said metallosilicate comprises a member of the pentasil family.

36. A process as claimed in claim 23 wherein the concentration of the organosilicon compound in said solvent is in the range of 2 to 50% by weight.

37. A process as claimed in claim 23 wherein the concentration of the organosilicon compound in said solvent is in the range of 5 to 25% by weight.

38. A process for preparing a catalyst composite said process comprising:
   a) contacting an intermediate pore metallosilicate with an organosilicon compound in a solvent for a specific duration and then recovering the solvent;
   b) drying the catalyst;
   c) repeating the steps a) and b) above;
   d) calcining the catalyst in an oxygen containing atmosphere sufficient to remove the organic material and deposit siliceous matter on the metallosilicate;
   wherein the said organosilicon compound is aminoalkyl trialkylsilane.

39. A process for preparing a catalyst composite said process comprising:
   a) contacting an intermediate pore metallosilicate with an organosilicon compound in a solvent for a specific duration and then recovering the solvent;
   drying the catalyst;
   c) repeating the steps a) and b) above;
   d) calcining the catalyst in an oxygen containing atmosphere sufficient to remove the organic material and deposit siliceous matter on the metallosilicate;
   wherein the said organosilicon compound is 3-aminopropyl triethoxysilane.

40. A process for preparing a catalyst composite useful for alkylaromatic conversion, the said process comprising:
   a) contacting an intermediate pore metallosilicate with an organosilicon compound in a solvent for a specific duration and then recovering the solvent;
   b) combining the organosilicon compound treated metallosilicate with water and then drying the catalyst;
   c) repeating the steps a) and b) above;
   d) calcining the catalyst in an oxygen containing atmosphere sufficient to remove the organic material and deposit siliceous matter on the metallosilicate;
   wherein the metallosilicate comprises a member of the pentasil family selected from the group consisting of: Ga-ZSM-5, Fe-ZSM-5, B-ZSM-5, Ga-Al-ZSM-5, Fe-Al-ZSM-5, B-Al-ZSM-5.

41. A process as claimed in claim 40 wherein said metallosilicate is Ga-Al-ZSM-5 having silicon to aluminium ratio in the range of 150 to 600 and silicon to gallium ratio is in the range of 500 to 2000.

42. A process for preparing a catalyst composite useful for alkylaromatic conversion, the said process comprising:
   a) contacting an intermediate pore metallosilicate with an organosilicon compound in a solvent for a specific duration and then recovering the solvent;
   b) combining the organosilicon compound treated metallosilicate with water and then drying the catalyst
   c) repeating the steps a) and b) above; and
   d) calcining the catalyst in an oxygen containing atmosphere sufficient to remove the organic material and deposit siliceous matter on the metallosilicate;
   wherein said metallosilicate is Ga-Al-ZSM-5 having silicon to aluminium ratio in the range of 150 to 600 and silicon to gallium ratio is in the range of 500 to 2000.

43. A process for preparing a composite comprising the said process comprising:
   a) contacting an intermediate pore metallosilicate with a water soluble organosilicon compound in a solvent and then recovering the solvent;
   b) drying the product from step a) at a temperature in the range of 10 to 150° C.;
   c) repeating the steps a) and b) above; and
   d) calcining the product in an oxygen containing atmosphere at a temperature in the range of 160 to 800° C. sufficient to remove the organic material and deposit siliceous matter on the metallosilicate;
   wherein in said process calcining step d) is not repeated multiple times after each of steps a)+b).

* * * * *